United States Patent [19]

Joa

[11] 4,094,319
[45] June 13, 1978

[54] SANITARY PAD WITH MULTIPLE END FOLDS

[76] Inventor: Curt G. Joa, Box 1121, Boynton Beach, Fla. 33435

[21] Appl. No.: 737,750

[22] Filed: Nov. 1, 1976

[51] Int. Cl.² .............................................. A61F 13/16
[52] U.S. Cl. ..................................... 128/284; 128/287
[58] Field of Search ................... 128/284, 287, 290 R, 128/296

[56] References Cited

U.S. PATENT DOCUMENTS

| | | | |
|---|---|---|---|
| 3,402,715 | 9/1968 | Liloia et al. | 128/287 |
| 3,585,999 | 6/1971 | Wanberg | 128/287 |
| 3,658,063 | 4/1972 | Schaar | 128/287 |
| 3,776,233 | 12/1973 | Schaar | 128/287 |
| 3,814,100 | 6/1974 | Nystrand | 128/287 |
| 3,844,288 | 10/1974 | Kiela | 128/287 |
| 3,930,501 | 1/1976 | Schaar | 128/287 |

*Primary Examiner*—John D. Yasko
*Attorney, Agent, or Firm*—Joseph P. House, Jr.

[57] ABSTRACT

A disposable diaper with an absorbent pad that is both narrower and shorter than the diaper back sheet has plural folds formed in opposing end margins of the back sheet overlapping the ends of the absorbent pad to reduce the length of the folded diaper to the approximate length of the absorbent pad without shortening the waistband, thereby stiffening the ends of the folded diaper, expediting the handling and packaging thereof, and reducing the size of the packages therefor.

5 Claims, 8 Drawing Figures

U.S. Patent
June 13, 1978
4,094,319
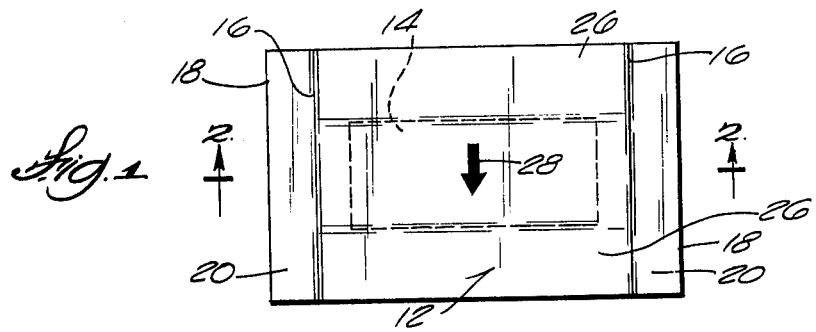
Fig. 1
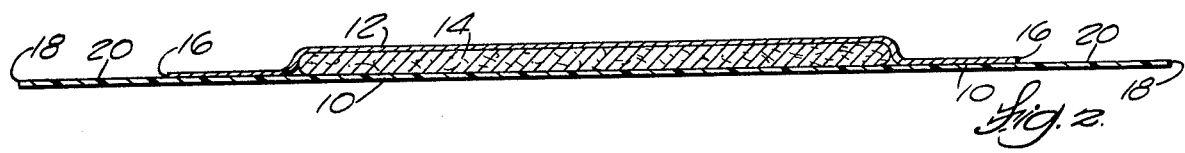
Fig. 2
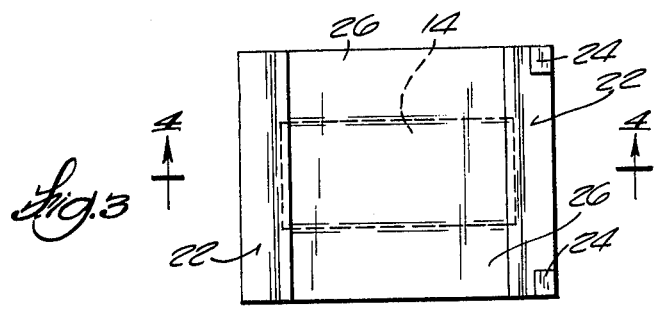
Fig. 3
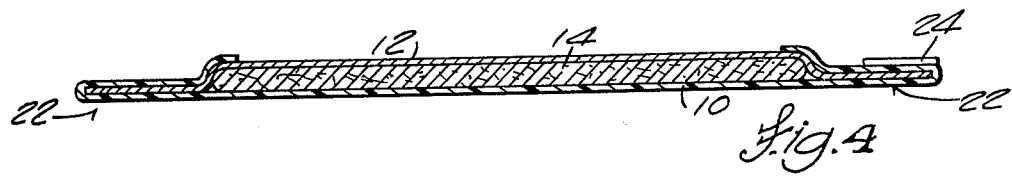
Fig. 4
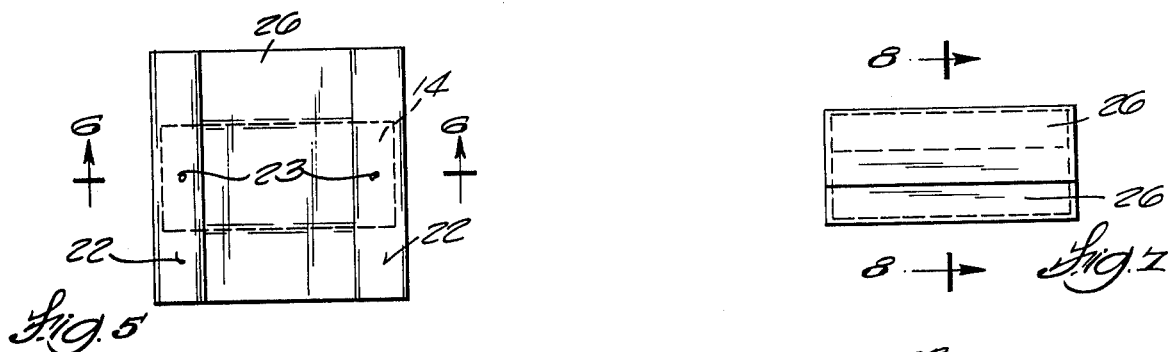
Fig. 5
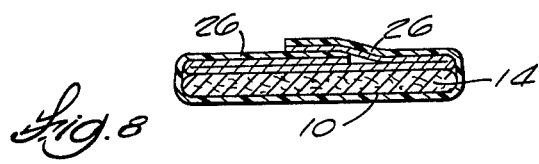
Fig. 7
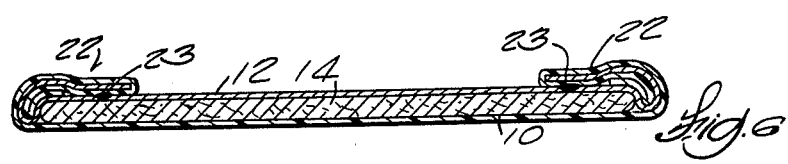
Fig. 6
Fig. 8

SANITARY PAD WITH MULTIPLE END FOLDS

BACKGROUND OF THE INVENTION

This invention relates to disposable sanitary pads such as diapers which have an absorbent pad that is both narrower and shorter than the diaper back sheet. The invention also relates to a method of manufacturing and packaging such sanitary pads. In the past, disposable diapers had an absorbent pad that was long enough to reach the top of the diaper waistband. The waistband was formed by folding the opposing end margins of the diaper back sheet inwardly over the ends of the absorbent pad to form a multiple thickness waistband in the portions of the back sheet and top sheet which extended laterally beyond the side margins of the absorbent pad. The folded-over portion of the back sheet and top sheet was fastened down with an adhesive to form a permanent fold which constituted the waistband. Inasmuch as the absorbent pad came to the top of the waistband, no trouble was encountered in folding the diaper for packaging or in packaging the diaper.

In recent years, however, new chemicals have been developed with increase the absorbency of such absorbent pads and thus permit the use of smaller pads. Accordingly, it is possible to shorten the absorbent pads to reduce the cost of the diapers. However, as the position of the waistband cannot be dropped to match the shortened pads without spoiling the fit of the diapers, the result is that a portion of the relatively thin and easily yieldable waistband projects beyond the ends of the absorbent pad after the diapers are folded for packaging in the conventional manner. This presents difficulty in handling and packaging the diaper and causes the portion of the waistband which projects beyond the ends of the absorbent pad to become crushed in the package.

SUMMARY OF THE INVENTION

In accordance with this invention, the above-noted problem has been solved by making multiple folds in the end margins of the diaper top sheet and back sheet overlapping the ends of the absorbent pad. This reduces the length of the folded diaper to the approximate length of the absorbent pad without shortening the waistband. This stiffens the ends of the folded diaper, expedites the handling and packaging thereof, eliminates crushing of the waistband, and reduces the size of the packages therefor.

DESCRIPTION OF THE DRAWINGS

FIG. 1 is a reduced scale plan view of a disposable diaper top sheet and back sheet spread out flat with an absorbent pad sandwiched therebetween.

FIG. 2 is an enlarged longitudinal sectional view taken on the line 2—2 of FIG. 1.

FIG. 3 is a reduced scale plan view of the disposable diaper of FIGS. 1 and 2 with the end margins thereof folded once inwardly and fastened down to form a waistband.

FIG. 4 is an enlarged longitudinal sectional view taken on the line 4—4 of FIG. 3.

FIG. 5 is a reduced scale plan view of the disposable diaper of FIGS. 1-4 with the end margins folded once more inwardly over the ends of the absorbent pad.

FIG. 6 is an enlarged longitudinal sectional view taken on the line 6—6 of FIG. 5.

FIG. 7 is a reduced scale plan view of the disposable diaper of FIGS. 1-6 with the side panels which project beyond the side edges of the absorbent pad folded thereover.

FIG. 8 is an enlarged cross sectional view taken on the line 8—8 of FIG. 7.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The drawings illustrate steps involved in manufacturing a disposable sanitary pad such as a diaper and preparing it for packaging in accordance with the method of this invention. In the particular example illustrated, the various steps are presumed to be carried out manually, although in most applications they are performed by automatic machinery such as disclosed in Joa U.S. Pat. No. 3,844,288. The application of this invention to automatic manufacturing and packaging machines will be discussed after the manual method illustrated in FIGS. 1-8 has been described.

The material for manufacturing disposable sanitary pads typically includes a moisture impervious plastic back sheet 10, a moisture permeable top sheet 12 made of non-woven fabric and an absorbent filler pad 14 of crepe wadding or fluffed pump. Pad 14 is both narrower and shorter than back sheet 10 and top sheet 12. This disclosure will relate specifically to disposable diapers, although the invention applies to other sanitary pad products such as sanitary napkins.

The developed diaper width is the vertical dimension in FIG. 1 and its developed length is the horizontal dimension in FIG. 1. Back sheet 10 and top sheet 12 have the same width, but back sheet 10 is desirably longer than top sheet 12 by an amount equal to approximately twice the width of the diaper's waistband. Absorbent pad 14 is centered on back sheet 10 in both dimensions and top sheet 12 is also centered thereon in both dimensions over pad 14 with the opposite end edges 16 of top sheet 12 being equidistant from the adjacent end edges 18 of back sheet 10. The portions of top sheet 12 which extend beyond the end and side edges of pad 14 may be secured to back sheet 10, broadly over thin facing surfaces by conventional adhesives, including those incorporated in the surface coating of the plastic back sheet 10.

After the major components of the diaper have been assembled as shown in FIGS. 1 and 2, either manually or by automatic machinery, the next step in manufacturing the diaper is to fold both end margins or panels 20 of back sheet 10 once inwardly over the adjacent end edge 16 of top sheet 12 and to fasten end panels 20 to top sheet 12 broadly over their facing surfaces with conventional adhesives as aforesaid to form a triple thickness waistband 22 on both ends of the diaper as shown in FIGS. 3 and 4. Pressure sensitive adhesive patches or tapes 24 covered by release liners are then applied to the corners of one of the waistbands 22 for fastening the waistband around a baby's waist. At this point, the diaper is ready to be folded for packaging.

The next step is to fold both waistbands 22 inwardly over the ends of absorbent pad 14, as shown in FIGS. 5 and 6. This reduces the length of the diaper to the approximate length of pad 14 without shortening waistband 22. This stiffens the ends of the folded diaper to expedite handling and packaging thereof, eliminates crushing of the waistband in the package and reduces the size of the packages. If necessary or desirable, the opposing end margins 20 of back sheet 10 can be folded inwardly more than twice.

With the plural folded diaper ends of this invention, the use of shortened absorbent pads 20 not only saves on pad cost, but also saves on packaging cost due to the reduction in the size of the individual diaper packages and in the cartons therefor.

The second fold in the end margins of the diaper is not broadly fastened down as is the outermost fold which forms waistband 22, inasmuch as the second fold and any succeeding folds are to be unfolded by the user before the diaper is placed on the baby. However, a temporary fastener such as one or more small breakaway adhesive dots 23 can be employed to temporarily hold the second and any succeeding folds in place during packaging.

The next folding step in preparation for packaging the diaper is to fold the side panels 26 inwardly over the sides of absorbent pad 14 in the conventional manner as shown in FIGS. 7 and 8, which disclose a conventional C-fold, other types of folds can be utilized. The diapers are then inserted into their packages either by hand or with automatic packing machinery with reduced danger of malfunction in the packaging machinery due to flexible ends which are eliminated in the method of this invention.

In manufacturing the diapers and folding them in automatic machinery, the arrow 28 in FIG. 1 indicates the machine direction with respect to the individual diapers. Back sheet 10 and top sheet 12 are portions of a continuous web which is not cut into diaper width pieces until after all folds have been made in the end margins of sheets 10 and 12 as shown in FIGS. 5 and 6. The long dimension of pads 14 are directed transverse to the machine direction 28 of the webs. All folds in the opposing end margins of sheets 10 and 12 are desirably and easily made in the side margins of the webs with conventional plow folders (not shown). Both webs are then cut transverse to the machine direction on both sides of pads 14 by a conventional web cutter (not shown) to separate the webs into individual diapers. The C-folds or other folds in the diaper side panels 26 are subsequently made with conventional automatic folding machinery (not shown) and the packaging is done with conventional automatic packaging machinery (not shown).

What is claimed is:

1. In a disposable sanitary pad which includes a top sheet, a back sheet, and an absorbent pad sandwiched therebetween, the absorbent pad being shorter and narrower than the back sheet, the improvement comprising plural folds in the opposing end margins of said back sheet and including corresponding first folds in which the end margins of the back sheet are doubled back over themselves to form waistbands extending beyond the ends of the absorbent pad and corresponding second folds in which the waistbands thus formed are folded back over the end margins of the absorbent pads, thus to reduce the length of the folded sanitary pad to the approximate length of said absorbent pad.

2. The disposable sanitary pad of claim 1 wherein the second folds are fastened together with breakaway adhesive so that they can be conveniently unfolded before the diaper is used.

3. The disposable sanitary pad of claim 1 wherein said back sheet is made of moisture impervious plastic material.

4. The disposable sanitary pad of claim 1 wherein said back sheet is longer than said top sheet by an amount approximately equal to twice the width of said waistband.

5. The disposable sanitary pad of claim 4 wherein said absorbent pad, top sheet, and back sheet are all rectangular, and where said absorbent pad and top sheet are both centered in both dimensions on said back sheet.

* * * * *